United States Patent [19]

Moll et al.

[11] Patent Number: 4,654,030

[45] Date of Patent: Mar. 31, 1987

[54] TROCAR

[75] Inventors: Frederic H. Moll, San Francisco; Alex T. Roth, Foster City, both of Calif.; Peter F. Costa, Cambridge; William A. Holmes, Marblehead, both of Mass.

[73] Assignee: Endotherapeutics, Redwood City, Calif.

[21] Appl. No.: 832,742

[22] Filed: Feb. 24, 1986

[51] Int. Cl.$^4$ .............................................. A61M 5/18
[52] U.S. Cl. .................................... 604/165; 604/272; 128/305
[58] Field of Search ............... 604/164, 165, 158, 169, 604/272–274; 128/305

[56] References Cited

U.S. PATENT DOCUMENTS

| | | | |
|---|---|---|---|
| 3,039,468 | 6/1962 | Price | 604/164 X |
| 3,090,384 | 5/1963 | Baldwin | 604/272 |
| 4,601,710 | 7/1986 | Moll | 604/165 |

Primary Examiner—Stephen C. Pellegrino
Attorney, Agent, or Firm—Ciotti & Murashige

[57] ABSTRACT

A trocar assembly consisting of a trocar tube subassembly and a separable, interfitting trocar subassembly is described. The trocar tube assembly includes a hollow body having a first front opening in which a trocar tube is mounted, a second rear opening for receiving the trocar subassembly, and a manually pivotable flap valve mechanism mounted within the body. The trocar subassembly includes a head having a central bore in which are mounted the (1) rear ends of an elongated obturator having a pyramidal-shaped piercing head with a triangular-shaped base, and a concentric tubular shield having a triangular shaped front opening for the piercing head that is formed by bevels in its leading edge that have approximately the same slope as the surfaces that define the three sides of the piercing head, and (2) a coil spring backing the shield for biasing the shield between retracted and extended positions. When the two subassemblies are fit together, the obturator and concentric shield extend through the hollow body with the front wall of the head fitting within a recess in the rear wall of the hollow body such that the trocar assembly cannot be rotated without disengaging the two subassemblies. The shield has a slot in its outer wall that is engaged by the flap valve to lock the shield in its extended position. The shield may be unlocked by pivoting the flap valve out of the slot, sliding the trocar assembly rearwardly so that the front wall of the head is clear of the recess in the rear wall of the hollow body, rotating the trocar subassembly to a position in which the flap valve and slot are not aligned and sliding the front wall of the trocar assembly back into the recess in the rear wall of the hollow body.

7 Claims, 8 Drawing Figures

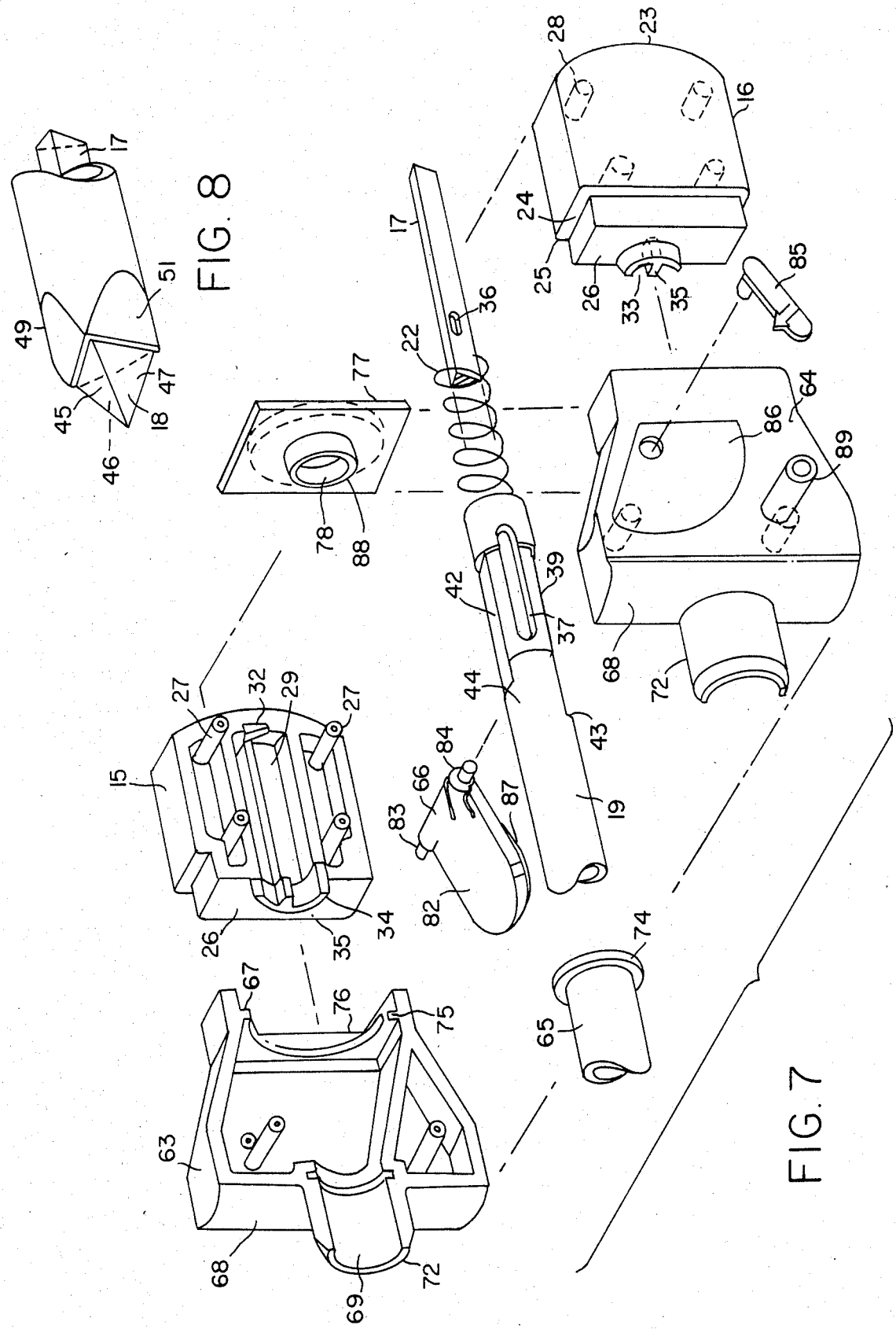

TROCAR

DESCRIPTION

1. Technical Field

The invention is in the field of surgical instruments. More particularly it concerns an improved trocar.

2. Background Art

Trocars are sharp-pointed instruments used to puncture a body cavity. This is often done so that fluids may be drained using a cannula inserted into the opening. Trocars are also used during endoscopic procedures. A conventional endoscopic procedure follows three steps. The first step is the insertion of a Veress cannula into the abdominal cavity through a small incision in the abdominal wall and the cavity is inflated with insufflating gas passed through the cannula. After inflation, the Veress cannula is removed. Finally, a standard trocar housed within the bore of a trocar tube is thrust into the inflated abdomen. Standard trocars are shaped like a large metal peg with a sharpenend point. The trocar is then removed and the endoscopic instrument is inserted into the abdominal cavity through the trocar tube.

Commonly owned U.S. patent application Ser. No. 638,048, filed Aug. 26, 1984 now U.S. Pat. No. 4,601,710 describes two embodiments of a trocar having a spring-bodied tubular protective shield. One embodiment shows a trocar whose piercing tip is formed of three blades. The shield of this trocar is a tubular body having a frustoconical end that is slotted to receive the blades. In the second embodiment—which was considered to be an improvement over the first—the piercing tip is pyramidal and is formed by three bevels in the end of an otherwise cylindrical body. The shield of this second embodiment is a tubular body having a circular opening that has a bevel on its leading edge that generally matches the slope of the pyramidal piercing tip. The second embodiment also has a shield locking mechanism that comprises a slide valve-actuated locking tooth that engages a slot in the wall of the shield. While both of these embodiments were operational, the cutting action of the first embodiment was not optimum and the operation of the slide valve locking mechanism on the second embodiment was cumbersome. Further, the force required to thrust the trocar into the abdomen in both embodiments was large. It was, therefore, desirable to improve the locking mechanism and design of the piercing tip. It was also desirable to provide an improve valve mechanism, as well.

DISCLOSURE OF THE INVENTION

The present invention provides a trocar that is improved over the above-described trocars with respect to the force required to thrust the trocar through the abdominal wall, the shield locking mechanism, and the sealing means for the trocar tube once the trocar has been withdrawn.

Accordingly, one aspect of the invention is an improvement in a trocar assembly comprising an elongate trocar obturator having a piercing tip at its front end, an elongate trocar tube in which the obturator is housed, a tubular protective shield mounted concentrically around the obturator and being axially movable relative to the obturator between a normally extended position and a retracted position, and biasing means acting on the rear end of the protective shield, whereby the shield is forced to said retracted position to expose the piercing tip when the trocar is being inserted through the wall of a body cavity and is biased by said means to said extended position to shield the piercing tip once the trocar has pierced the wall, in which the piercing tip has a pyramidal cutting head that has a triangular base and the protective shield has a triangular-shaped opening to receive said head said opening being formed by the bases of three generally parabolically shaped bevels in the front edge of the shield and being in general registry with the base of the head when the shield is in said retracted position.

BRIEF DESCRIPTION OF THE DRAWINGS

FIG. 7 is a exploded partial view of the trocar of FIG. 1.

FIG. 8 is an exploded view of the tip portion of the trocar showing the shield in its retracted position.

MODES FOR CARRYING OUT THE INVENTION

Figure 3:
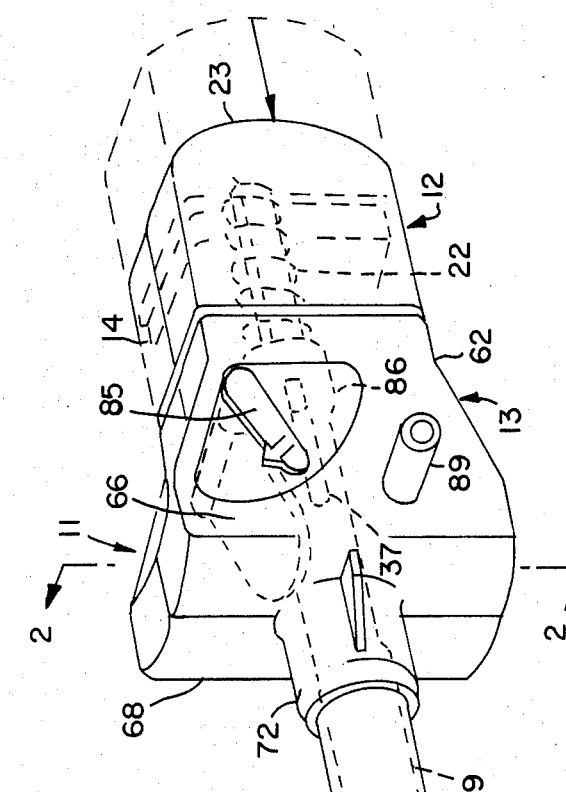
FIG. 3 is an enlarged exploded view of the tip portion of the trocar of FIG. 1.
Figure 3:
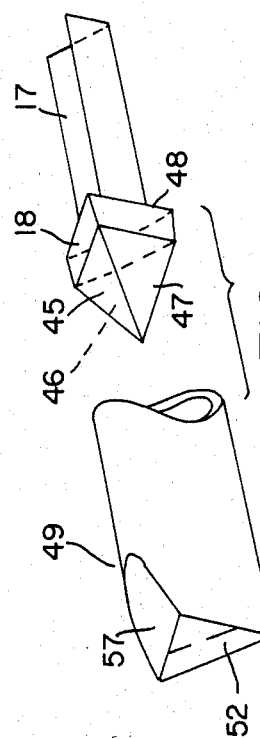

The drawings illustrate a trocar assembly, generally designated 11, that is basically composed of two parts: a trocar subassembly 12 and a trocar tube subassembly 13. The two subassemblies are interfitting, but designed to be separable from each other. Referring to FIG. 7, the basic elements of the trocar subassembly are a head or grip 14 composed of halves 15 and 16; an obturator 17 having a piercing tip 18; a generally tubular obturator sleeve or shield 19; and a spring 22 for biasing the shield.

Figure 2:
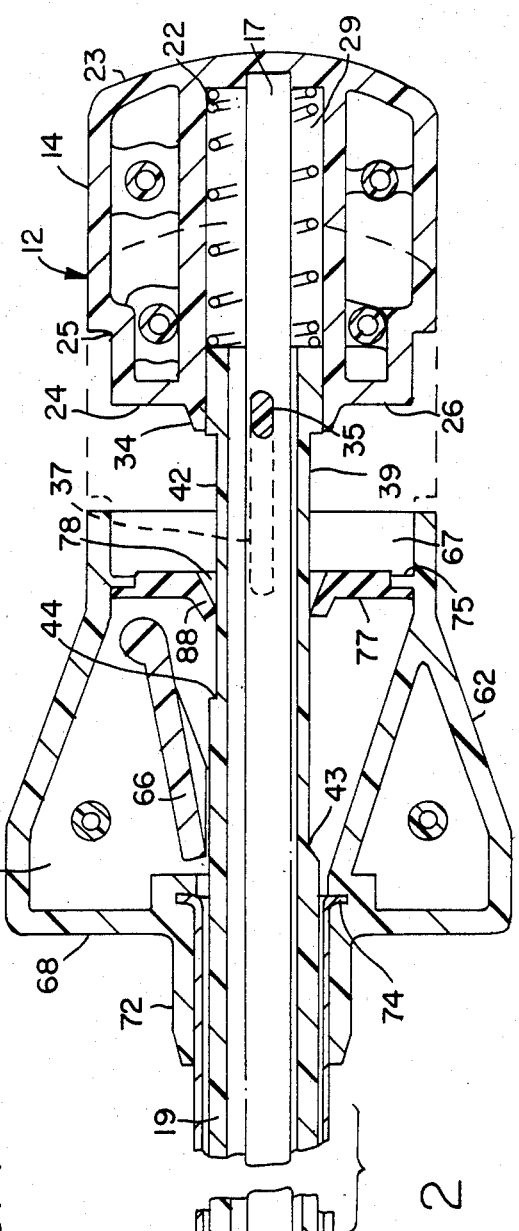
FIG. 2 is an enlarged sectional view of the trocar of FIG. 1 taken along line 2—2 of FIG. 1.
Figure 5:
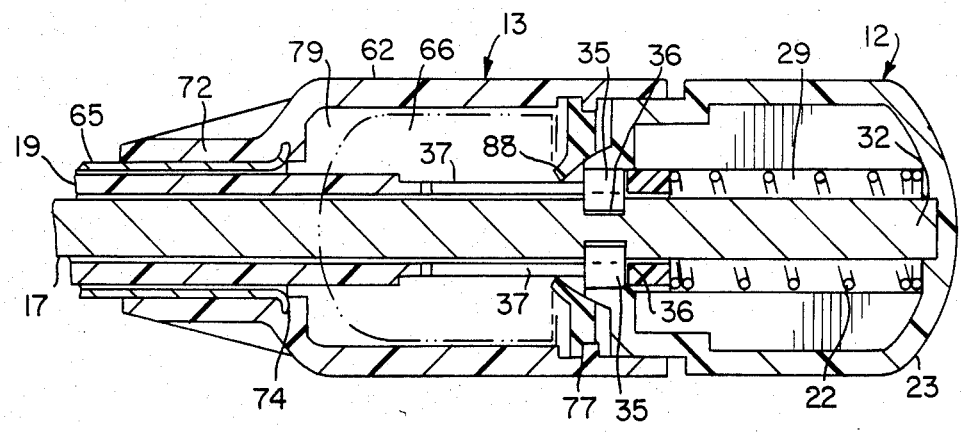
FIG. 5 is a sectional view taken along line 5—5 of FIG. 4.
Figure 4:
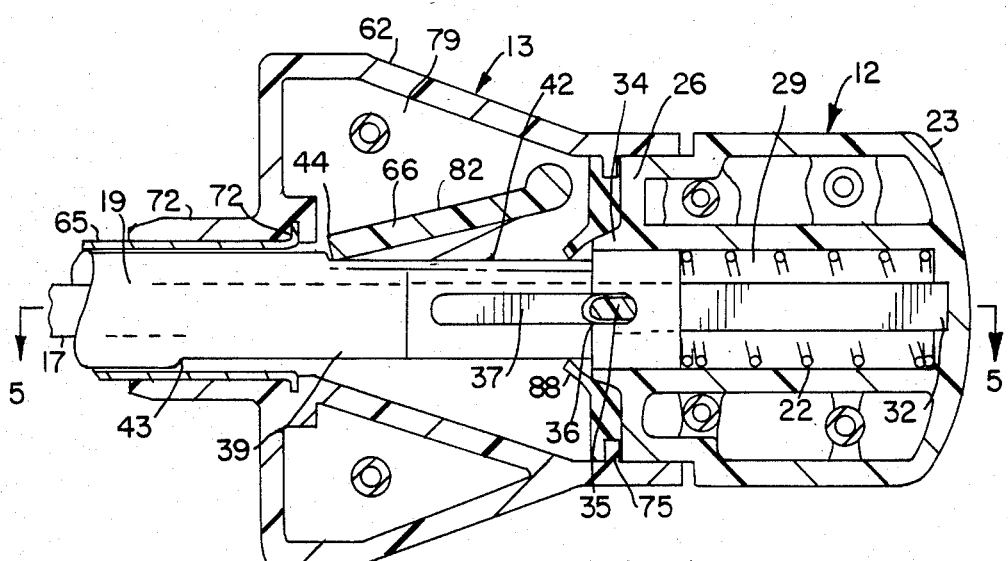
FIG. 4 is an enlarged sectional view of the head portion of the trocar showing the obturator-shield subassembly in a locked position within the head.
Figure 6:
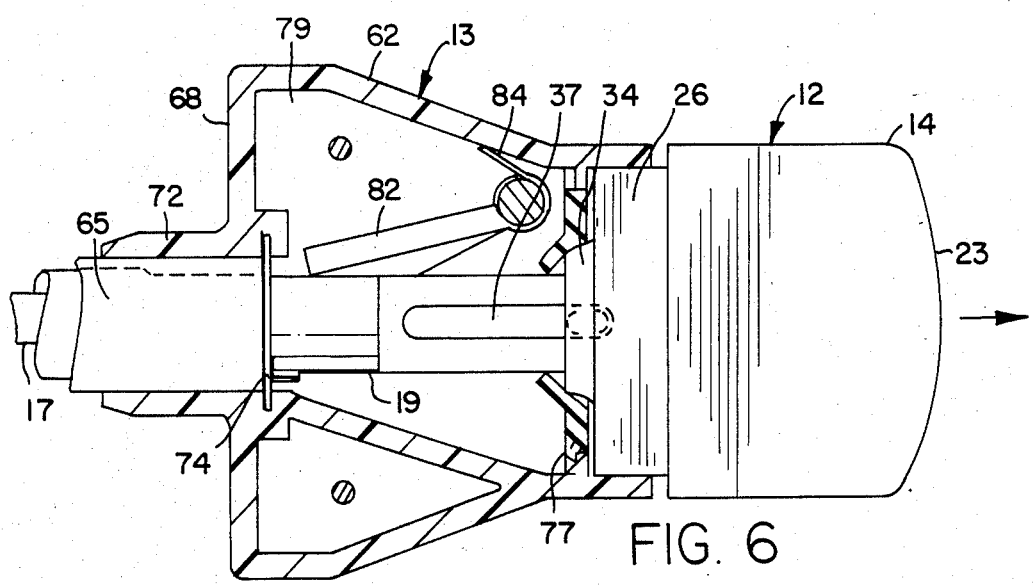
FIG. 6 is a partial enlarged sectional view of the head portion of the trocar showing the obturator-shield subassembly in an unlocked position.

Head 14 has a rounded rear wall 23 that fits comfortably into the palm of the hand and a generally rectangular front wall 24. Wall 24 has a shoulder 25 that defines an inward raised section 26. The two halves 15 and 16 are generally symmetrical and snap fit together with the four posts 27 extending transversely from the inner wall of half 15 into the corresponding four tubular stands 28 extending transversely from the inner wall of half 16 (see FIG. 7). The head has a central axial bore 29 for receiving the obturator and shield. Bore 29 terminates in a triangular-shaped depression 32 formed in the inner face of the rear wall into which the rear end of the obturator shaft fits to prevent rotation of the obturator (See FIG. 2). The front wall 24 has a circular opening 33 that is defined by a collar 34 and opens into the axial bore. The inner surface of each of the collar halves carries a key 35. The keys 35 fit into keyways 36 in the rear end of the obturator shaft to securely fasten the obturator shaft to the grip. The rear end of the tubular shield has a pair of diametrically opposed axially elongated openings 37 in which the keys ride to permit axial movement of the shield relative to the obturator shaft. As shown in FIGS. 2, 4, and 5, the spring 22 sits around the rear end of the obturator shaft with its ends seated against the inner face of the rear wall of the grip and the rear end wall of the shield.

The rear end of the obturator shield has a reduced diameter segment 38 that begins just forwardly of the forward ends of the openings 37. The rear end of the shield also has a pair of diametrically opposed axially elongated slots 39 and 42 that are displaced 90° relative to the openings 37. Both slots terminte rearwardly at the shoulder that defines the forward transition to the reduced diameter segment. Slot 39 is longer than 42 and its leading edge 43 is sloped to provide a smooth transition to the normal diameter surface of the shield. The shorter slot 42 has a generally flat transverse leading edge 44 which, as described in detail below, serves as a stop in locking the shield so as to prevent relative axial movement between it and the obturator.

Figure 1:
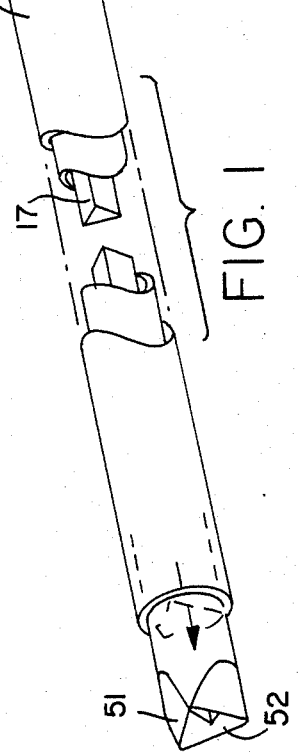
FIG. 1 is an isometric view of an embodiment of the improved trocar of the invention.

As depicted in FIGS. 1 and 7, the shaft of the obturator is triangular in cross section. Its leading end terminates in pyramidal piercing tip 18. The tip is formed from three generally equilateral triangular surfaces 45, 46, and 47 whose junctions form three sharp cutting edges. The tip has a triangular base 48. The leading end 49 of the shield has three sets of inner and outer bevels 51 that form an opening 52 of triangular cross section just slightly larger than that of the base of the tip to permit the tip to extend out the end of the shield (FIGS. 1, 3, and 8). The bevels in the outer surface of the shield have substantially the same slopes as the surfaces 45, 46, and 47 and act as extensions of the surfaces 45, 46 and 47 when the shield is retracted (FIG. 8) and provide a smooth transition between the tip and the shield. The combination of the correspondence between the shape of the leading end of the shield and the piercing tip and the smooth transition markedly reduces the force required to insert the trocar into body cavities relative to the thrust required to insert the earlier versions of the trocar described above. As shown, the bevels are generally parabolically shaped and their bases define the triangular opening in the end of the shield. When the shield is retracted (FIG. 8) the base of the tip is in registry with the opening 52.

The principal elements of the trocar tube subassembly 13 are: a main body 62 composed of two generally symmetrical halves 63, 64 (FIG. 7) that are held together by fastening means; an axially elongated trocar tube 65; and a flap valve mechanism 66. The rear end of body 62 has a rectangular recess 67 that mates with the raised section 26 on the front end of the grip of the trocar subassembly when the two subassemblies are interfitted. The front wall 68 of the body is curved to facilitate gripping the trocar with the fingers and has an circular opening 69 defined by a collar 72 in which the trocar tube is mounted. The collar has a circumferential groove 73 at its rear end into which a collar 74 on the rear end of the trocar tube is seated to fix the tube within the collar 72. The rear wall 75 of the body has a central circular opening 76 in which a rubber grommet 77 is seated. Grommet 77 has a central oening 78 through which the trocar subassembly may be inserted/withdrawn. The body has an inner cavity 79 into which the openings 69 and 78 open and in which the flap valve mechanism is mounted. The flap valve mechanism includes a U-shaped flapper 82, a shaft 83 that traverses the cavity and on which the flapper is carried, a spring 84 about one end of the shaft, and an actuating lever 85 carried on one end of the shaft exteriorly of the body. The exterior of the body at the location of the lever has a fan-shaped recess 86 in which the lever moves.

The flap valve mechanism serves two functions in the operation of the trocar assembly. First, it acts in combination with the shield as a shield locking means. Secondly, it acts as a closure means when the trocar subassembly is withdrawn and separated from the trocar tube subassembly. In this latter regard, the rear side of the flapper carries a circular pad 87 made of a deformable seal-forming material such as plastic (e.g., Tygon TM), rubber or the like that fits against grommet 77 when the subassemblies are separated.

The trocar assembly operates and is used as follows. Before use the trocar will typically be in the assembled form shown in FIGS. 1 and 2 with the raised rectangular section 26 fitting into the recess 67 and the trocar obturator and shield inserted through the opening in the grommet 77, the cavity 79 of the trocar tube subassembly, and the lumen of the trocar tube 65. The trocar shield will normally be locked in its extended position as seen in FIGS. 4 and 5 for safety purposes and for storage. In this position the piercing tip is shielded and cannot be damaged by inadvertent contact with other surfaces. In this locked position the spring 22 biases the trocar tube forwardly with the rear edges of the openings 37 acting as stops for the keys 35 to define the forwardmost position of the shield. The shield is positioned with its short slot 42 facing the flapper with the edge of the flapper lodged against the leading edge 44 of the slot, thereby preventing rearward movement of the shield. The spring 84 of the mechanism biases the flapper inwardly to keep the flapper lodged securely in this position. Also as seen in FIG. 4 the inner lip 88 surrounding the grommet opening rests snugly against the perimeter of the rear end of the shield and forms a seal therewith.

In order to unlock the shield, the actuating lever of the mechanism is pivoted manually so as to disengage the edge of the flapper from the slot. As long as lever 85 is held in its pivoted position, it allows the shield to retract and extend. When lever 85 is released, spring 84 returns it to its original position. In this original position lever 85 acts as a latch which locks the shield when it returns to its extended position. When lever 85 is pivoted, the trocar subassembly may be drawn rearwardly until the raised section 26 clears the recess 67. In an alternate or "won't lock" mode of operation, when lever 85 is pivoted, the trocar subassembly may then be rotated 180° so that the long slot 39 of the shield faces the flapper. The trocar subassembly is then pushed forwardly to once more seat the raised section 26 within the recess 67. In this position the flapper does not impede rearward movement of the shield against the force of the spring 22 to expose the piercing tip. Thus, the shield is free to move in both the retracting and extending directions. The rearwardmost position of the shield in its unlocked mode is again defined by the stopping action of the keys 35 in the openings 37.

The trocar is inserted through the tissue defining the wall of the body cavity while the shield is free to retract either because the flapper has been disengaged manually by moving lever 85 or because its trocar assembly has been rotated 180 into the "won't lock" position. In practice, this insertion is made through a small incision through the skin. The trocar is gripped firmly in the hand with the rear wall of the head against the palm and the index and middle fingers extending around the front wall of the trocar tube body on either side of the tube.

The leading end is placed against the incision in the skin and pressure is exerted against the skin. This pressure causes the the shield to be pushed rearwardly against the spring 22 to its retracted position (shown in FIG. 8), thereby exposing the piercing tip. The tip enters the incision and underlying tissue with continued pressure. Once the tip has penetrated the tissue and has entered the cavity the force against the front end of the shield ceases and the shield is automatically moved axially back to its extended position through the action of spring 22. So long as lever 85 is not being held in its pivoted or latch release position, and the trocar is not in the "won't lock" mode, the shield will automatically lock in its extended (protecting) position. Viscera and other internal tissues are thus protected from contact with the piercing tip and potential damage therefrom. Although this locking will not take place if lever 85 is held in its pivoted or "tripped" position or if the device is in the "won't lock" mode, the force of spring 22 will hold the shield in its extended position and give substantial protection, nonetheless.

The trocar subassembly may be withdrawn from the trocar tube subassembly once the cavity has been penetrated. In this operation, once the leading end of the trocar assembly clears the opening 78 in the grommet, the spring 84 will bias the flapper pad into contact with the inner side of the grommet thus closing the opening 78. Air pressure within the body cavity is thus maintained. In this regard the half 64 of body 62 is equipped with a stopcock port 89 into which the nozzle of a stopcock (not shown) is inserted. The stopcock will normally be closed during the trocar insertion to maintain the gas pressure within the body cavity. If necessary, the stopcock may be used as a conduit for passing additional insufflating gas into the cavity.

After the trocar subassembly has been separated from the trocar tube assembly, surgical instruments may be inserted into the body cavity via the trocar tube assembly to view internal tissues, perform operations thereon, or drain body fluids. Latch 85 can be used to manually open valve 66 to facilitate such activities and also permit the removal of specimens and to deflate the cavity.

Modifications of the above described modes of carrying out the invention that are obvious to those of skill in the fields of mechanical engineering, surgical instrument design or related fields are intended to be within the scope of the following claims.

What is claimed is:

1. In a trocar assembly comprising an elongate trocar obturator having a piercing tip at its front end, an elongate trocar tube in which the obturator is housed, a tubular protective shield mounted concentrically around the obturator and being axially movable relative to the obturator between a normally extended position and a retracted position, and biasing means acting on the rear end of the protective shield, whereby the shield is forced to said retracted position to expose the piercing tip when the trocar is being inserted through the wall of a body cavity and is biased by said means to said extended position to shield the piercing tip once the trocar has pierced the wall, the improvement wherein the piercing tip has a pyramidal cutting head that has a triangular base and the protective shield has a triangular-shaped opening to receive said head said opening being formed by the bases of three generally parabolically shaped bevels in the front edge of the shield and being in general registry with the base of the head when the shield is in said retracted position.

2. The trocar assembly of claim 1 wherein the assembly includes means for reversibly locking the shield in said extended position.

3. The trocar assembly of claim 2 including the further improvement wherein the means for reversibly locking the shield in said extended position includes a manually operable pivotable flap valve housed within a hollow body having a first opening in which the trocar tube is mounted and a second opening through which the obturator and shield extend and a slot in the exterior wall of the shield positioned such that the flap valve may be pivoted to engage the slot whereby retraction of the shield is prevented and pivoted out of engagement with the slot whereby said retraction is permitted.

4. The trocar assembly of claim 3 including second biasing means acting on the flap valve to pivot the flap valve into engagement with the slot.

5. The trocar assembly of claim 4 wherein the second biasing means pivots the flap valve to a position that closes said second opening when the obturator and shield are withdrawn from the trocar tube and the hollow body.

6. The trocar assembly of claim 4 including means for manually pivoting the flap valve out of engagement with the slot and wherein the second biasing means automatically pivots the flap valve into engagement with the slot when the shield is extended thereby automatically preventing additional retraction.

7. The trocar assembly of claim 3 wherein the shield can be rotated into a second position in which the slot does not align with the flap valve such that locking engagement between the flap valve and the slot is not possible.

* * * * *